(12) United States Patent
Chandran et al.

(10) Patent No.: US 6,890,957 B2
(45) Date of Patent: *May 10, 2005

(54) LIQUID FORMULATION OF METFORMIN

(75) Inventors: Ravi Chandran, Bolton Landing, NY (US); Ashish Gogia, New Delhi (IN)

(73) Assignee: Ranbaxy Laboratories Limited, New Delhi (IN)

( * ) Notice: Subject to any disclaimer, the term of this patent is extended or adjusted under 35 U.S.C. 154(b) by 127 days.

This patent is subject to a terminal disclaimer.

(21) Appl. No.: 10/382,442

(22) Filed: Mar. 6, 2003

(65) Prior Publication Data

US 2003/0149111 A1 Aug. 7, 2003

Related U.S. Application Data

(63) Continuation of application No. 09/923,491, filed on Aug. 7, 2001, now Pat. No. 6,559,187.
(60) Provisional application No. 60/223,391, filed on Aug. 7, 2000.

(51) Int. Cl.$^7$ .............................................. A61K 31/24
(52) U.S. Cl. ....................................... 514/634; 514/635
(58) Field of Search ................................ 514/634, 635

(56) References Cited

U.S. PATENT DOCUMENTS

| | | |
|---|---|---|
| 3,174,901 A | 3/1965 | Sterne et al. ................. 167/65 |
| 3,174,921 A | 3/1965 | Matheson .................... 204/162 |
| 4,379,785 A | 4/1983 | Weyer et al. ................ 424/244 |
| 4,572,912 A | 2/1986 | Yoshioka et al. ........... 514/369 |
| 4,639,436 A | 1/1987 | Junge et al. .................. 514/24 |
| 4,904,769 A | 2/1990 | Rauenbusch ............... 536/17.2 |
| 5,594,016 A | 1/1997 | Ueno et al. .................. 514/369 |
| 5,614,492 A | 3/1997 | Habener ....................... 514/12 |
| 6,031,004 A | 2/2000 | Timmins et al. ............. 514/635 |

FOREIGN PATENT DOCUMENTS

| | | | |
|---|---|---|---|
| EP | 0 177 303 | 5/1990 | ............ A61K/7/16 |
| EP | 0 373 103 | 3/1993 | .......... A61K/31/19 |
| WO | WO 99/55320 | 11/1999 | .......... A61K/31/55 |
| WO | WO 02/11716 | 2/2002 | ......... A61K/31/155 |

*Primary Examiner*—Rebecca Cook
(74) *Attorney, Agent, or Firm*—Jayadeep R. Deshmukh, Esq.; George E. Heibel, Esq.

(57) ABSTRACT

The present invention is directed to a liquid formulation of metformin or its pharmaceutically acceptable salts thereof. The liquid pharmaceutical composition comprises a therapeutically effective amount of metformin or its pharmaceutically acceptable salt, in a liquid carrier, which may also include a sweetener that does not increase the blood glucose level of a subject after ingestion thereof. In one embodiment, it may also include alkyl hydroxyethylcellulose, and/or a polyhydroxy alcohol. In another embodiment, the carrier may contain a sweetener, mineral acid, and bicarbonate salt maintained at a pH of 4.0 to 9.0. It is useful for treating hyperglycemia and diabetes.

15 Claims, No Drawings

LIQUID FORMULATION OF METFORMIN

CROSS REFERENCE TO RELATED APPLICATION

This application is a continuation of U.S. patent application Ser. No. 09/923,491 filed on Aug. 7, 2001, now issued as U.S. Pat. No. 6,559,187, and is claiming the benefit of U.S. Provisional Application Ser. No. 60/223,391, filed on Aug. 7, 2000.

FIELD OF THE INVENTION

The present invention relates to a liquid formulation of metformin and salts thereof and to the use thereof in treating hyperglycemia and/or diabetes.

BACKGROUND OF THE INVENTION

Diabetes Mellitus is the most common of the serious metabolic diseases affecting humans. It has been estimated that there are over 200 million people that have diabetes in the world.

Metabolically, diabetes is characterized by an inappropriate elevation of blood glucose levels. In Type I Diabetes Mellitus, this is due to an absence of insulin in the individual. In Type II Diabetes Mellitus, although there is circulating insulin, its signal is not efficiently transduced via the insulin receptor, giving rise to insulin resistance, where the body responds less and less well to a given amount of insulin. Insulin is a peptide hormone which is produced by the Langerhorn islets in the pancreas. Insulin triggers increased glucose utilization, protein synthesis, and the formation and storage of neutral lipids. The present invention focuses on Type II Diabetes Mellitus, or non-insulin-dependent diabetes.

Diabetes Mellitus is also characterized by long term complications involving the eyes, nerves, kidneys and blood vessels. These diabetic complications include premature atherosclerosis, intercapillary glomerulosclerosis, retinopathy and neuropathy. The major cause of morbidity and mortality among diabetics is coronary heart disease.

The primary goal in the treatment of diabetes is to maintain blood glucose levels as close to normal as possible. For Type II diabetics, the first line of therapy for maintaining blood glucose level is modification of diet and lifestyle. The diabetic diet features restrictions on fat content and an increased intake of dietary fiber. Regular exercise is also emphasized to decrease weight and reduce the degree of insulin resistance.

If diet and lifestyle modifications fail to control glucose levels, oral hypoglycemic therapy or insulin therapy is required to control glucose levels and thus minimize complications related to the disease.

One of the compounds used to treat diabetes is metformin or its pharmaceutically acceptable salts. Metformin is a dimethyl biguanide having the formula:

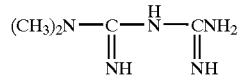

The pharmaceutically acceptable salts of the formula

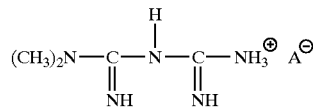

in which A is the anion of the non-toxic salt are the preferred medicaments.

U.S. Pat. No. 3,174,921 to Sterne discloses various pharmaceutically acceptable salts of metformin, for example, phosphate, sulfate, hydrochloride, salicylate, maleate, benzoate, ethanedisulfonate, fumarate and glycolate. U.S. Pat. No. 6,031,004 to Timmins, et al. discloses metformin salts of dibasic acids, such as fumarate and succinate, wherein the molar ratio of metformin:dibasic acid is 2:1.

However, the most preferred metformin product is the hydrochloride salt. In fact, the biguanide anti-hyperglycemic agent, metformin, is currently marketed in the U.S. in the form of its hydrochloride salt. (Glucophage®, Bristol-Myers Squibb Company).

Metformin hydrochloride is a cohesive white powder which is highly soluble in water (>300 mg/ml at ambient temperature). The market metformin hydrochloride salt has a pronounced saline, bitter taste. Accordingly, it is usually marketed as a coated tablet wherein its coating is masked or is designed to mask any unpleasant taste.

Unfortunately, as sold, the tablet is very large, making it different to swallow. Moreover, due to its size, this drug cannot be used by children or adults who are not able to swallow tablets. However, the present inventors realize that a liquid formulation would be useful for children and adults who cannot swallow large size tablets or orally intake chewable tablets.

To date, no one has heretofore made a liquid formulation of metformin hydrochloride salt which has masked the unpleasant taste thereof. Moreover, to date, no one has made a liquid formulation of metformin or salt thereof.

The preparation of a liquid formulation for masking the bitter taste of metformin or its salts is not straightforward, as one might think. After all, the skilled artisan would expect that the taste could be masked by adding a sugar. However, since the liquid formulation is being used to treat diabetes, sugar cannot be used. Moreover, in addition to being sugar free, the liquid formulation should contain none or a minimal amount of sodium salt since it detrimental to diabetic patients. Moreover, it should contain little or no alcohol (ethanol) since ethanol is detrimental to diabetic patient. Furthermore, metformin and its salts, especially the hydrochloride salts are so bitter, it has heretofore been difficult to completely mask the taste without the use of sugar, alcohol and sodium salts.

The present inventors have also found a means of making the metformin in the liquid formulation palatable to patients.

SUMMARY OF THE INVENTION

The present invention is directed to a liquid pharmaceutical composition for oral administration to a subject in need thereof which comprises a therapeutically effective amount of metformin or a pharmaceutically acceptable salt thereof in association with a pharmaceutically acceptable liquid carrier.

In a preferred embodiment, the present invention is directed to a liquid formulation of metformin or its pharmaceutically acceptable salts, wherein the formulation comprises a therapeutically effective amount of metformin in a liquid carrier, containing a sweetener or polyhydroxy alcohol. In one preferred embodiment, the liquid carrier contains at least one of the following components: a polyhydroxy alcohol, a sweetener that does not raise the alcohol sugar level when ingested by a mammal, or an alkyl hydroxyethylcellulose. In a more preferred embodiment, the liquid formulation of the present invention contains at least two of the additional components and most preferably all three additional components. It is most preferred, in this embodiment, that the liquid formulation comprises a therapeutically effective amount of metformin or its pharmaceutically acceptable salts, about 40% to about 80% by weight of a sweetener, about 5% to about 55% by weight polyhydroxy alcohol and about 0.01% to about 5% by weight alkyl hydroxyethylcellulose.

In another embodiment, the liquid formulation comprises a therapeutically effective amount of metformin or its pharmaceutically acceptable salt, a sweetener or mixture of sweeteners that do not raise the alcohol sugar level when ingested by a mammal, and a mineral acid and bicarbonate salt, such that the pH of the formulation ranges from about 4 to about 9. In this formulation, the acid and bicarbonate salt are present in an amount sufficient to maintain the formulation in a pH ranging from about 4.0 to about 9.0. In this embodiment, it is preferred that the sweetener is a mixture of a sugar alcohol and non-nutritive sugar.

The present invention is also directed to a method of treating hyperglycemia which comprises administering to a patient in need of treatment an antihyperglycemic effective amount of said liquid formulation. In another embodiment, the present invention is directed to a method for treating Type II diabetes in a patent which comprises administering to a patent in need of treatment an anti-diabetic effective amount of said liquid formulation.

DETAILED DESCRIPTION OF THE INVENTION

As used herein, the term "patient" refers to an animal who is suffering from hyperglycemia or diabetes. The preferred animal is a mammal, such as dogs, cats, horses, cows and humans. It is preferred that the patient is a human.

As described hereinabove, an aspect of the present invention is directed to a liquid formulation comprising a therapeutically effective amount of metformin or its pharmaceutically acceptable salts in association with a liquid carrier.

Metformin and various pharmaceutically acceptable salts are described in U.S. Pat. Nos. 3,174,901 and 6,031,004, the contents of which are incorporated by reference. Examples include mono and dibasic acid salts of metformin, including the hydrochloride salt, the phosphate salts, sulfate salts, hydrobromide salts, salicylate salts, maleate salt, benzoate salt, succinate salt, ethane disulfonate salt, fumarate salt, glycolate salt and the like. The pharmaceutical composition of the present invention contains a therapeutically effective amount of metformin or its pharmaceutically acceptable salts thereof. By "therapeutically effective amount" of metformin is meant that amount of metformin or its pharmaceutically acceptable salt which either maintains or reduces the concentration of sugar in the blood of the patient, depending upon the severity of the disease. The therapeutically effective amount is determined by an ordinarily skilled artisan, taking into account various considerations, such as the age of the subject, the weight of the subject, the condition of the patient, the type of patient (i.e., the type of animal), the regimen, the desired result and the like. The amount prescribed is determined by physicians, who may adjust the dosage regime received by the patients. For example, several divided dosages may be administered daily or the dose may be proportionally reduced as indicated by the exigencies of the therapeutic situation. For example, in a preferred embodiment, the metformin or its pharmaceutically acceptable salts are administered to the patient in amounts as described for the hydrochloride, as set forth in the Physician's Desk Reference. Preferably, a therapeutic effective amount of metformin or salt thereof ranges from about 10 mg/kg/day to about 40 mg/kg/day and more preferably from about 14 mg/kg/day to about 38 mg/kg/day. The liquid formulation of the present invention contains a therapeutically effective amount of metformin or its pharmaceutically acceptable salts. Preferably, the liquid formulation contains metformin or its pharmaceutically acceptable salts in an amount ranging from about 20 mg/ml to about 400 mg/ml and more preferably from about 40 mg/ml to about 200 mg/ml and, most preferably, from about 50 mg/ml to about 100 mg/ml.

The metformin, or its pharmaceutically acceptable salts are in association with a liquid carrier. The liquid form, as contemplated by the present invention, include solutions, suspensions, syrups and emulsions and only suspension (e.g., mix formulation in oily liquid vehicle). Inasmuch as the pharmaceutical composition is for oral administration, the liquid carrier is one that is normally utilized as a liquid carrier in pharmaceutical formulations and preparations, except that the liquid carrier should not contain excessive alcohol (ethanol). The ethanol, if present, is present in minimal amounts, e.g., no more than about 1% (v/v) or more preferably no more than about 0.5% (v/v). The liquid carrier may be an aqueous liquid, such as water, a non-aqueous liquid, such as glycols, e.g., propylene glycol or polyethylene glycol, vegetable oil, an oil-in-water emulsion or a water-in-oil liquid emulsion, or an aqueous dispersion, such as in glycol, liquid polyethylene glycol, vegetable oil and mixture thereof. The preferred liquid carrier is water.

It is preferred that the liquid formulation of the present invention is syrupy. It is even more preferred that the viscosity of the liquid formulation is near or greater than 1. Inasmuch as the liquid formulation flows, the upper limit is the maximum viscosity that a flowing liquid can have. It is preferred that the viscosity of the liquid formulation of the present invention ranges from about 5 to about 50 cps, and more preferably, from about 10 to about 40 cps, and more preferably, from about 15 to about 35 cps and most preferably about 25 cps. Moreover, it is preferred that the density of the liquid formulation of the present invention is one g/mL or greater, with the maximum value being that value a flowing liquid can have. It is preferred that the density of the liquid at 25° C. is between 1 g/mL and 2 g/mL and more preferably between 1.05 g/mL and 1.5 g/mL and more preferably between 1.1 g/mL and 1.3 g/mL.

In a first embodiment, the present liquid formulation comprises the metformin or its pharmaceutically acceptable salts thereof, the liquid carrier and at least one or two of the following: a sweetener, a polyhydric alcohol, an alkyl hydroxy ethyl cellulose, or combination thereof. It is most preferred that it contains all three components.

As indicated herein above, in this embodiment, the liquid formulation preferably contains polyhydric alcohols. The term polyhydric alcohol means any organic polyalcohol containing more than one hydroxy group thereon. It includes propylene glycol, dipropylene glycol, polyethylene glycol, glycerin, butylene glycol, hexylene glycol, polyoxyethylene, polypropylene glycol, sorbitol or other sugar alcohol, ethylene glycol and the like. When the polyhydric alcohol is a polymer, such as polyethylene glycol, it is preferred that the number of hydroxy groups thereon is about the same as the number of carbon atoms present. If not a polymer, it is preferred that the alkyl moiety contains 2 to 6 carbons and 2 to 6 hydroxy groups. Such polyhydric alcohols include glycols, triols and polyols having 2, 3, 4, 5 to 6 alcoholic hydroxy groups per molecule or per repeating unit of the polymer. Typical of said glycols are glycols containing 2 to 10 carbon atoms, e.g., ethylene glycol, propylene glycol, butylene glycol and polyethylene glycol (average molecular weight ranging from about 200 to about 8000 daltons and more preferably from about 200 to about 6000 daltons), and most preferably from about 200 to about 2000 daltons, and the like. Examples of said triols include glycerin, trimethylol propane, and the like. Other examples of polyols include sorbitol, polyvinyl pyrrolidone, and the like. In this embodiment, however, it is preferred that the polyol is not a sugar (carbohydrate) or sugar alcohol; it is preferred that the polyhydroxy alcohols are glycols, triols, or polymers and the like, e.g., alkanes or polymers comprised of repeating alkylene units, wherein the alkanes or repeating alkylene units in the polymers are substituted by at least 3 to 6 hydroxy groups. These polyhydric alcohols may be used either singly or in combination. If used in combination, it is preferred that two or three different polyhydric alcohols are used. The most preferred polyhydric alcohol is polyethylene glycol, preferably having a molecular weight ranging from about 200 daltons to about 2000 daltons and more preferably from about 400 daltons to about 1600 daltons. A polyethylene glycol having a molecular weight greater than 1000 daltons provides the syrupy texture that is preferably desired in the formulation of the present invention and is effective in masking the bitter taste of metformin and its salts. However, as the molecular weight of the polyethylene glycols increases, it becomes more and more viscous and the liquid containing same becomes thicker and more difficult with which to work. At the higher molecular weights, the polyethylene glycol begins to adopt more solid-like properties. Furthermore, the greater the molecular weight the less of the polyethylene glycol used in the formulation. Thus, it is preferred that the polyethylene glycol when present is a mixture of polyethylene glycol of 1000 daltons or less and a polyethylene glycol greater than 1000 daltons. It is within the skill of one ordinary skill in the art to mix the various types of polyethylene glycols to obtain a liquid formulation of desired viscosity, especially having a viscosity within the ranges and preferred ranges indicated herein above.

The polyhydric alcohols are present in amounts in the liquid formulation ranging from about 5 to about 55% by weight and, more preferably, from about 15 to about 40% by weight and most preferably from about 20% to about 30% by weight. If polyethylene glycol is the polyhydric alcohol, it is preferred that it is a mixture of polyethylene glycol having a molecular weight greater than 1000 daltons and 1000 daltons or less. Moreover it is preferred that the weight ratio of polyethylene glycol of 1000 daltons or less to the polyethylene glycol of greater than 1000 daltons ranges from about 1:1 to about 6:1 and more preferably from about 5:1 to about 4:1 and most preferably from about 1:2:1 to about 3:1. It is preferred that the weight ratio of polyhydric alcohol to sweetener, if present, ranges from about 1:1 to about 6:1 and, more preferably, from about 1.5:1 to about 4:1 and, most preferably, from about 2:1 to about 3:1.

In addition, the weight ratio of polyhydric alcohol to alkyl hydroxyethyl-cellulose, if present, ranges from about 50:1 to about 400:1 and more preferably from about 100:1 to about 400:1, and most preferably, from about 200:1 to about 300:1.

The weight ratio of metformin or its pharmaceutically acceptable salt to polyhydric alcohol preferably ranges from about 1:2 to about 4:1, and more preferably from about 1:1 to about 3:1, and most preferably from about 1.5:1 to about 2:1.

In this first embodiment, the liquid formulation preferably contains a sweetener (i.e., a compound that imparts a sweet taste but does not increase the blood glucose levels of the patient). Examples include a sugar alcohol and non-nutritive sugars.

As used herein, the term sugar alcohol refers to reduced sugars. The preferred sugar alcohol are mono-saccharide alcohols and disaccharide alcohols. The monosaccharide alcohols have the formula $HO-CH_2(CHOH)_n-CH_2OH$, wherein n is 2–5. They also include tetritols, pentitols, hexitols and heptitols. Examples of sugar alcohols include erythritol, theritol, ribitol, arabinitol, xylitol, allitol, dulcitol, glucitol, sorbitol, mannitol, altritol, iditol, maltitol, lactitol, isomalt, hydrogenated starch hydrolysate and the like. The sugar alcohols, especially the monosaccharide alcohols, may be utilized as a racemic mixture or in the D or L form.

The non nutritive sweeteners are patentably sweet but are non-caloric. Examples include L-sugars, aspartame, alitame, acesulfame-K, cyclamate, stevioside, glycyrrhizin, sucralose, neohesperidin, dihydrochalcone, thaumatin saccharin and its pharmaceutically acceptable salts (e.g., calcium), and the like.

In this embodiment of the present formulation, it is preferred that the sweetener be present in the liquid formulation in amounts ranging from about 40% to about 80% by weight and more preferably from about 50% to about 70% and most preferably from about 55% to about 65%. In addition, it is preferred that the weight ratio of sweetener to alkyl hydroxyethyl cellulose, when present, ranges from about 400 to about 800, and, most preferably, from about 500 to about 600.

In this embodiment, the ratio of sweetener to metformin or its pharmaceutically acceptable salt ranges from about 8:1 to about 1:1, and, more preferably, from about 6:1 to about 2:1 and, most preferably, from about 5:1 to about 3:1.

Another component that is preferably present in the first embodiment of the liquid formulation of the present invention is an alkyl hydroxyethylcellulose. This is produced stepwise or by simultaneous reaction of ethylene oxide and a hydrophobic alkylating reagent known in the art. As used herein, with respect to this term, the alkyl group contains preferably from 1 to 24 carbon atoms and more preferably from 2 to 15 carbon atoms, and most preferably, from 2 to 10 carbon atoms. Examples include ethylhydroxy ethyl cellulose (EHEC) manufactured by Berol Kemi AB under the Bermocoll trade name and hydroxy ethyl cellulose (HEC), modified with a long chain alkyl group, generally termed HMHEC (HM=Hydrophobically Modified) manufactured by Aqualon Cot sold under the trade name Natrosol Plus, and the like.

The alkyl hydroxyethylcellulose, when present in this embodiment, is present in the liquid formulation in an amount ranging from about 0.01 to about 5% by weight, and more preferably from about 0.05 to about 1% by weight and most preferably from about 0.08 to about 0.2% by weight. The weight ratio of alkyl hydroxyethylcellulose, when present, to metformin or its pharmaceutically acceptable salt ranges from about 1:300 to about 1:50 and more preferably, from about 1:200 to about 1:100.

In this first embodiment, it is preferred that the liquid formulation of the present invention contains metformin or its pharmaceutically acceptable salts, the sweetener, the alkyl hydroxyethylcellulose and the polyhydroxy alcohol in association with the liquid carrier, in the amounts described herein.

In a second embodiment, the pharmaceutical liquid formulation of the present invention contains the metformin in pharmaceutically effective amounts as described hereinabove and the liquid carrier, as defined hereinabove. In addition, the pharmaceutical liquid formulation also contains a sweetener, as defined hereinabove. The sweetener is present in an amount ranging from about 10% to about 70% of the liquid formulation and more preferably is present in an amount ranging from about 20% to about 60% and most preferably from about 30% to about 50% (w/w). It is most preferred that the sweetener in this embodiment is a mixture of two sweeteners, a sugar alcohol, as defined hereinabove and a non-nutritive sweetener, as defined hereinabove. It is preferred that the sugar alcohol is present in amounts greater than the non-nutritive sweetener. More preferably, the weight ratio of the sugar alcohol to non-nutritive sweetener preferably ranges from about 700:1 to about 85:1 and more preferably ranges from about 300:1 to about 100:1 and more preferably from about 200:1 to about 110:1.

In addition, it is preferred in this embodiment that the weight ratio of metformin to sweetener ranges from about 1:35 to about 1:1 and more preferably from about 1:20 to about 1:10 and most preferably from about 1:15 to about 1:5.

Besides the sweetener, and the metformin and the liquid carrier, it is preferred that the pH of the formulation is about 4.0 or greater. The present inventors have found that when the pH is greater than about 4.0, the bitter taste of the metformin is greatly reduced. However, the formulation cannot be too basic for at high pH's, it may be harmful to the animal or mammal. It is preferred that the pH ranges from about 4.0 to about 9.0 and more preferably from about 4.2 to about 7.0 and most preferably ranging from about 4.3 to about 5.1.

Base and/or acid may be added to the formulation to control the pH.

However, it is most preferred that the acid is a mineral acid, that is, it completely dissociates when placed in water at 25° C. Examples include e.g., hydrochloric acid, sulfuric acid, nitric acid and the like. Hydrochloric acid is the most preferred. Although HCl(g) may be dissolved in the liquid formulation, it is preferred that hydrochloric acid be utilized.

The base that is utilized is a bicarbonate salt. Any bicarbonate salt which is not toxic or harmful especially to diabetics can be used. The preferred salts are potassium salts.

Without wishing to be bound, it is believed that the mineral acid and bicarbonate salts present with the metformin, causes in-situ formation and release of effervescent gas (carbon dioxide, which carbonation helps in the taste masking of metformin liquid in pH range of about 4.0 to about 9.0 and more preferably in the desired pH ranges indicated hereinabove, along with the sugar alcohol and non-nutritive sweetener.

The pharmaceutical liquid formulation of the present invention may, in addition contain optional ingredients. For example, the liquid formulation comprising metformin or its pharmaceutically acceptable may include another antihyperglycemic agent.

The metformin or salt thereof may be in combination with one or more antihyperglycemic agents. Moreover, the metformin alone or in combination with one or more antihyperglycemic agents may also be employed in combination with amylin.

The antihyperglycemic agent may be an oral antihyperglycemic agent, e.g., a sulfonyl urea, such as glyburide (also known as glibenclamide), glimepride (disclosed in U.S. Pat. No. 4,379,785, the contents of which are incorporated by reference), glipizide, gluclazide, or chloropropamide or other known sulfonyl ureas or other antihyperglycemic agents which act on the ATP-dependent channel of the B cells. The preferred sulfonylurea are glyburide and glipizide.

Where present, the sulfonyl ureas, such as glyburide, glimepiride, glipyride, glipizide, chlorpropamide and gliclazide and the glucosidase inhibitors acarbose or miglitol may be employed in formulation amounts and dosing as indicated in the Physician's Desk Reference.

The metformin or salt thereof is preferably employed in a weight ratio to the sulfonylurea in the range from about 50:1 to about 300:1, and more preferably, from about 75:1 to about 250:1.

The antihyperglycemic agent may also be a glucosidase inhibitor, such as acarbose (disclosed in U.S. Pat. No. 4,904,769, the contents of which are incorporated by reference) or miglitol (disclosed in U.S. Pat. No. 4,639,436, the contents of which are incorporated by reference).

The metformin or salt thereof is preferably employed in a weight ratio to the glucosidase inhibitor within the range from about 2:1 to about 300:1 and more preferably from about 25:1 to about 200:1.

The antihyperglycemic agent may be a thiazolinedione oral anti-diabetic agent (which has an insulin sensitivity effect in patents with Type II diabetes) such as troglilitazone (Warner Lambert's Rezulin®, disclosed in U.S. Pat. No. 4,572,912, the contents of which are incorporated by reference), zorglitazone (Smith-Kline Beecham), pioglitazone (Takeda) Mitsubishi's MCC-555 (disclosed in U.S. Pat. No. 5,594,016, the contents of which are incorporated by reference), Glaxo-Welcome's GL-262570, englitazone (CP-68722 Pfizer) or darglitazone (CP-86325, Pfizer).

The metformin or salt thereof is preferably employed in a weight ratio to the thiazolidinedione in an amount within the range from about 0.1:1 to about 75:1 and more preferably from about 0.5:1 to about 5:1.

Where present, the thiazolidinedione anti-diabetic agent may be employed in amounts within the range from about 0.01 to about 2000 mg/day which may be administered in single or divided doses one to four times per day.

The metformin or salt thereof may also be employed in combination with a non-oral antihyperglycemic agents such as insulin or with glucagon-like peptide-1 (GLP-1) such as GLP-1(1–36) amide, GLP-1(7–36) amide, GLP-1(7–37) (as disclosed in U.S. Pat. No. 5,614,492 to Habener, the disclosure of which is incorporated herein by reference).

Where present insulin may be employed in formulations, in the amounts and dosing as indicated by the Physician's Desk Reference.

Where present GLP-1 peptides are administered in the liquid oral formulation of the present invention.

Other optional ingredients which may be present in the liquid formulations of the present invention include buffers, such as citric acid or its corresponding salts or acetic acids and its salts; flavoring agents, such as peppermint, oil of wintergreen, orange, or cherry flavoring, and the like, surfactants, thickeners, preservatives, such as methyl and propyl parabens, and the like; anti-oxidants, such as benzoate salts, and the like; chelating agents, such as EDTA and its salts and the like.

It is preferred that the liquid formulation is buffered having a pH ranging from about 4.0 to about 9.0 and more preferably from about 4.2 to about 7.0 and most preferably from about 4.3 to about 5.1. These pH ranges may be effected by one of ordinary skill in the art using conventional buffer systems, such as critic acid and citrate, and the like.

In addition, in accordance with the present invention, a method is provided for treating hyperglycemia including Type II diabetes (NIDDM) comprising administering to a patient in need thereof a liquid pharmaceutical composition comprising metformin or its pharmaceutically acceptable salts, in accordance with the present invention.

The liquid formulation of the present invention may be prepared by any of the known methods of pharmacy, but all methods include the step of bringing into association the metformin or the salt thereof, and optionally, the sweetener or mixture of sweeteners, if present, the alkyl hydroxyethylcellulose and the polyhydroxy alcohol or acid and base and the optional ingredients, with the liquid carrier. In general, the pharmaceutical compositions are prepared by uniformly and intimately mixing these various components with the liquid carrier. For example, aqueous solutions suitable for oral use can be prepared by dissolving the aforementioned and desired components in water and adding, if desired, additional optional ingredients such as suitable colorants, flavors, stabilizing and thickening agents, and the like, as desired. Aqueous suspensions suitable for oral use can be made by dispersing the finely divided metformin or its pharmaceutically acceptable salt and the desired components, e.g., the sweetener or mixture of sweetening, if present the acid and/or base, if present, the polyhydroxy alcohol, if present, the alkyl hydroxy ethyl cellulose, if present, and the other optional ingredients in water with viscous material normally used in the pharmaceutical arts to make dispersions, such as natural or synthetic gums, resins, methylcellulose, sodium carboxyethylcellulose and other well-known suspending agents.

It is to be understood that the ingredients used in the present formulation are non-toxic.

Unless indicated to the contrary, it is to be understood that the percentages are by weight. Moreover, it is to be understood that the percentages are of the dry weight of the formulation, excluding the weight of the liquid carrier. For example, if the carrier is water, it represents the dry weight of the formulation.

However, inasmuch as these formulations are to be administered to diabetics, the formulation does not contain sugars such as glucose, sucrose, and the like, which would increase the blood glucose levels of the patients. Moreover, in a preferred embodiment, the formulation of the present invention does not contain sodium salts. Furthermore, the liquid pharmaceutical composition of the present invention contains at most, minimal alcohol that is about 1% (v/v) or less and more preferably 0.5% (v/v) or less.

In addition, the singular denotes the plural and vice versa.

Furthermore, the terms polyhydroxy alcohol and polyhydric alcohol, as used herein, are synonymous, and are used interchangeably without changing the meaning.

Moreover, unless indicated to the contrary, the liquid carrier is relatively purified. For example, if water is the carrier, it is purified (distilled water) or deionized water.

The following examples further illustrate the present invention.

EXAMPLE 1

In a suitable manufacturing Tank, 60 liters of USP purified water was heated to 40° C. Throughout the process described hereinbelow, the temperature was maintained at 40° C. 1.9 kg. of polyethylene glycol was heated to 40° C. and Natrosol 250 HX, i.e., hydroxyethylcellulose, (142.5 g) was added to the polyethylene glycol in small quantities and mixed for 30 minutes at 40° C. at 60 revolutions per minute on a MagneTek mixer Model #6-962653-41 until homogeneous. The resulting mixture was added slowly to the water in the tank and the contents were mixed at 40° C. Metformin HCL (19 kg) was slowly added to the Tank at 60 RPM, while the temperature was maintained at 40° C. Calcium saccharin (1.188 kg) was added slowly to the tank and the contents were mixed for 10 minutes at 40 RPM. Citric acid (114 g) was added to the tank maintained at 40° C. and the contents were mixed at 40 RPM. Potassium benzoate (211.28 g) was added to the tank maintained at 40° C. and the contents were mixed at 40 RPM for 10 minutes. Additional polyethylene glycol (9.5 kg) was added slowly to the tank maintained at 40° C. and the contents were mixed for 30 minutes at 60 RPM. A 70% solution of sorbitol (in water) (w/w) (76 kg) was pumped slowly to the tank maintained at 40° C. and the contents were mixed for 20 minutes at 40 RPM. Additional polyethylene glycol (21.85 kg) was pumped into the tank and the contents were mixed for 20 minutes at 40 RPM. Cherry flavor (190 g) was added to the tank and the contents were mixed for 20 minutes at 40 RPM. The contents of the tank were cooled to 30° C., and additional water was added until the volume is 190 liters. The contents were additionally mixed at 30° C. for 60 minutes at 30 RPM.

The resulting product is a metformin hydrochloride liquid formulation.

The liquid formulation of the present invention containing metformin or its pharmaceutically acceptable salt has several advantages over a solid formulation containing metformin or its pharmaceutically acceptable salts. As a solid, the tablet containing same is quite large and is difficult to swallow. On the other hand, the liquid formulation is easy to swallow and administer. Unlike the solid formulation, the liquid formulation can be administered to children and adults who have difficulty swallowing large size tablets. Thus, the liquid formulation facilitates patient compliance.

Moreover, the present inventor has found that the liquid formulation of the present invention is unexpectedly safer and potentially exhibits less adverse effects than if the metformin or its salts were in a different formulation. For example, as described in the following examples, when the liquid formulation of metformin hydrochloride prepared in accordance with the present invention were given to fasting patients, the fasting bioavailability of the liquid formulation of the present invention was lower than that of the solid formulation by over 15%. This is surprising since it is expected that, under normal circumstances, when a drug substance in a tablet or capsule formulation is converted into a liquid solution, the bioavailability of such liquid formulation is usually no worse than that of the solid dosage form. For example, as shown hereinbelow in Example 3, when the liquid and tablet formulations of metformin hydrochloride were given to patients who were fed, there was very little difference between the bioavailability of the drug of either formulation. This was what one of ordinary skill in the art would also have expected.

One skilled in the art would also have expected no difference between the bioavailability of the liquid formulation of the metformin hydrochloride and the tablet of the metformin hydrochloride in the patient who did not, for some reason, take the medication with food. However, this was not what was observed, for the bioavailability was about 15% less in the liquid formulation. Consequently, in the case of the tablet there is a greater amount of the formulation absorbed when administered as a solid than as a liquid formulation in the fasting diet.

Metformin has numerous side effects associated with it. For example, diabetic patients, especially those with advanced age and reduced renal function, are at greater risk when ingesting metformin in solid form, rather than in liquid form, to suffer from lactose acidosis, which is fatal in 50% of the time. Moreover, cardiovascular collapse (shock), acute congesitive heart failure, acute myocardial infection and other conditions characterized by hypoxemia have been associated with lactose acidosis. Furthermore, these diabetic patients are at more risk of developing hypoglycemia when ingesting metformin in solid form. Moreover, those fasting patients who ingest the tablets are at greater risk of developing gastrointestinal reactions, such as diarrhea, nausea, vomiting, abdominal bloating, flatulence and anorexia—the side effects thereof. In other words, if the patient neglects to take the solid formulation with food, the patient is at greater risk to experience the detrimental side effects than if the patient were taking the liquid formulation of the present invention. This is attributable to the fact that more of the metformin or salt thereof in the solid formulation is absorbed in the blood-stream of the fasting patient than in the liquid formulation. Consequently, the fasting diabetic patient is more prone to experience the side effects when the drug is administered as a solid formulation than as a liquid.

The bioavailability results of the non-fasting patient and the fasting patient of both the solid and liquid formulations are indicated in Examples 2 and 3, respectively.

EXAMPLE 2

The metformin hydrochloride liquid formulation was prepared as in Example 1. A single oral dose of 5 mL of a 100 mg/mL test metformin HCL liquid solution followed with 240 mL of water, or one (1) reference 500 mg Glucophage® tablet (tablets of metformin hydrochloride) with 240 mL of water was administered to healthy male volunteers on two separate occasions separated by at least a one (1) week washout period. Water was provided ad libitum until 1.0 hour pre-dose. Fluid intake was controlled and consistent for 1.0 hour following drug administration as follows: Drug was given with 240 mL of room temperature water. Water was allowed ad libitum after 1.0 hour post-drug.

The subjects fasted for at least 10 hours prior to drug administration. However, thirty (30) minutes prior to drug administration, the subjects ingested a standard high-fat content breakfast which was completely consumed five (5) minutes prior to drug administration. The standard high-fat content breakfast consisted of the following: one (1) egg (fried), one (1) buttered English muffin, one (1) slice of American cheese, one (1) slice of Canadian bacon, one (1) serving of hash brown potatoes, eight (8) fluid ounces (240 ml) of whole milk and six (6) fluid ounces (180 ml) of orange juice. At 4.5 hours and 9.5 hours post-drug administration, standardized xanthine-free meals were provided to all subjects with a non-caffeine containing beverage. A snack was provided at 14.0 hours post dose.

All meals and beverage were xanthine-free and caffeine-free and were identical throughout each study period.

Seventeen (17) blood samples were drawn for drug content analysis within one hour prior to dosing (0.0 hour) and after dosing at 0.5, 1.0, 1.5, 2.0, 2.5, 3.0, 3.5, 4.0, 4.5, 5.0, 6.0, 8.0, 10.0, 12.0, 16.0 and 24.0 hours, during each study period. In addition, blood-glucose concentrations was measured using a glucometer at the following time-points: 0.0 (pre-drug) 1.0, 2.0, 3.0, 4.0, 6.0 and 8.0 hours post-drug. A total of 356.5 mL of blood was taken, including the amount for pre-study clinical blood tests. Upon completion of the clinical portion of the study, the plasma samples were analyzed.

The subjects were monitored throughout the confinement portion of the study.

Bioequivalence between formulation was evaluated based on the statistical comparisons of the area under the plasma metformin concentration versus time curves (AUC) and peak concentrations using standard techniques.

The results are tabulated hereinbelow:

TABLE 1

Mean Pharmacokinetic Parameters for Plasma Metformin HCl 100 mg/ml liquid.

| Parameter | Current Liquid Fed, 5 ml (100 mg/ml) Mean +/− SD | Glucophage ® Fed, 1 × 500 mg Mean +/− SD |
|---|---|---|
| AUC 0-t (ng · hr/mL) | 5240.18 ± 828.06 | 5180.71 |
| AUC 0-inf (ng · hr/mL) | 5467.24 ± 830.69 | 5389.42 ± 1090.07 |
| Cmax (ng/mL) | 749.29 ± 131.02 | 757.12 ± 175.95 |

| | Current Liquid vs. Glucophage ® | | |
|---|---|---|---|
| | AUC (0-t) | AUC (0-inf) | Cmax |
| 90% Geometric C.I. | 92%–114% | 93%–114% | 89%–114% |
| Ratio of Means | 103% | 103% | 100% |
| CV | 9.61% | 9.48% | 11.63% |

EXAMPLE 3

Study with Fasting Subjects

The liquid formulation of metformin hydrochloride was prepared as described in Example 1. A single oral dose of 5 mL of a 100 mg/mL test metformin HCl liquid solution followed with 240 mL of water, or one 500 mg Glucophage® tablet (sold by Bristol Meyers Squibb, tablet of metformin hyrdrochloride) with 240 mL of water was administered to 6 healthy fasting volunteers on two separate occasions separated by at least a one (1) week washout period. Water was provided ad libitum until 1.0 hour pre-dose. Fluid intake was controlled and consistent for 1.0 hour following drug administration as follows: Drug was given with 240 mL of room temperature water. Water was allowed ad libitum after 1.0 hour post-drug.

The subjects fasted for at least 10 hours prior to drug administration. At 4.5 hours and 9.5 hours post-drug, standardized xanthine-free meals were provided to the subjects with a non-caffeine containing beverage. In addition, a snack was provided at 14.0 hours post-drug.

All meals and beverages were xanthine-free and caffeine-free and were identical throughout each study period. Seventeen (17) blood samples were drawn for drug content analysis within one hour prior to dosing and after dosing at 0.5, 1.0, 1.5, 2.0, 2.5, 3.0, 3.5, 4.0, 4.5, 5.0, 6.0, 8.0, 10.0, 12.0, 16.0 and 24.0 hours, during each study period. In addition, blood-glucose concentrations were measured using a glucometer at the following time-points: 0.0 (pre-drug), 1.0, 2.0, 3.0, 4.0, 6.0 and 8.0 hours post-drug. A total of 356.5 mL of blood was taken, including the amount for pre-study clinical blood tests. Upon completion of the clinical portion of the study, the plasma samples were analyzed.

The subjects were monitored throughout the confinement portion of the study.

Bioequivalence between formulations was evaluated based on the statistical comparisons of the area under the plasma metformin concentration versus time curves (AUC), and peak concentrations ($C_{max}$) using standard techniques. The results are tabulated hereinbelow.

TABLE 2

Drug: Metformin HCl (n = 6)
Mean Pharmacokinetic Parameters for Plasma Metformin HCl 100 mg/ml liquid.

| Parameter | Current Liquid Fasting, 5 ml (100 mg/ml) Mean +/− SD | Glucophage ® Fasting, 1 × 500 mg Mean +/− SD |
|---|---|---|
| AUC 0-t (ng · hr/mL) | 5938.35 ± 1660.72 | 6860.95 ± 1052.70 |
| AUC 0-inf (ng · hr/mL) | 6093.20 ± 1665.57 | 7019.43 ± 1030.41 |
| Cmax (ng/mL) | 1011.79 ± 345.82 | 1173.64 ± 237.96 |

Current Liquid vs. Glucophage ®

| | AUC (0-t) | AUC (0-inf) | Cmax |
|---|---|---|---|
| 90% Geometric C.I. | 72%–99% | 73%–99% | 72%–97% |
| Ratio of Means | 85% | 85% | 83% |
| CV | 16.43% | 15.85% | 15.73% |

The variation between fed and fasting data for the liquid and tablet are summarized in the following table:

TABLE 3

| Parameters | Current Liquid Formulation | Glucophage ® |
|---|---|---|
| % Difference in AUC (0-t) Fed Vs Fasting (ng · hr/mL) | 13.32% | 32.43% |
| % Difference in AUC (0-inf) Fed Vs Fasting (ng · hr/mL) | 11.45% | 30.25% |
| % Difference in Cmax Fed Vs Fasting (ng/mL) | 35.09% | 55.09% |

Thus, the data in the tables clearly show that the liquid formulation of metformin and/or its pharmaceutically acceptable salts is an extremely useful form for the pediatric and old diabetic patients as well as those who find it difficult to swallow the large size pills of Glucophage® tablets the usual size going up to 1000 mg. Hence, a sizable diabetic patient community will be benefited by the liquid option. However, the most important benefit of the liquid formulation over the solid formulation is exhibited by the variation between the fasting and fed bioavailability, which is much less at around 10% in the liquid formulation compared to around 30% in solid formulation.

EXAMPLES 4–6

Three different metformin hydrochloride liquid formulations were prepared as follows:

| Ingredients | EXAMPLE 4 (pH 4.5) | EXAMPLE 5 (pH 8.0) | EXAMPLE 6 (pH 4.0 to 9.0) |
|---|---|---|---|
| 1. Metformin HCl | 100 mg/mL | 100 mg/mL | 100 mg/mL |
| 2. Xylitol | 40% w/v | 40% w/v | 40% w/v |
| 3. Potassium Bicarbonate | 5 mg/mL | 10 mg/mL | 5 mg/mL |
| 4. Potassium Sorbate | 0.12 w/v | 0.12% w/v | — |
| 5. Sodium Saccharin | 2.75 mg/mL | — | — |
| 6. Saccharin Calcium | — | 6.25 mg/mL | 3.5 mg/mL |
| 7. Hydrochloric Acid (Conc.) | 0.004 mL/mL | — | 0.004 mL/mL |
| 8. Wild Cherry Flavor | 0.275% w/v | — | — |
| 9. Art Cherry 349 Flavor | — | 0.4% v/v | 0.4% v/v |
| 10. Purified water | q.s. | q.s. | q.s |
| Total Weight | 500 g | 500 g | 500 g |

Under continuous stirring, potassium bicarbonate and metformin hydrochloride were added to purified water and dissolved to get a clear solution. Hydrochloric acid solution was added as a dilute solution (approx. 1 molar) to the mixture of the previous step. This results in carbon dioxide gas formation (effervescent gas). Next, xylitol was added and stirring was continued at a temperature of not more than 31° C., to get a clear solution. Stirring was continued and artificial cherry flavor and saccharin calcium was added. The pH was adjusted between the range of 4.6–4.9 using dilute solution of hydrochloric acid (if required). Purified water was added to make up the required volume and the mixture was filtered through clarifying grade filter and filled in approved packs with induction seal.

This process enables the formation of clear syrup formulation at pH 4.3–5.1 using combination of xylitol and saccharin calcium along with potassium bicarbonate.

EXAMPLE 7

The metformin hydrochloride liquid formulations of Example 4 (500 mg, 5 mL) and Example 1 (500 mg, 5 mL) were compared with the commercial product Glucophage®, a solid tablet of metformin hydrochloride (500 mg). These products were given to fasting subjects, in accordance with the protocol described in Example 3.

The 500 mg of Glucophage® or 5 mL of Example 1 or Example 4 were administered to the fasting test subjects.

The results are as follows:

| | $C_{MAX}$ | AUC0-t | AUC0-inf. |
|---|---|---|---|
| Ratio of Metformin in Product of Example 1 to Glucophage ® | 80 | 80 | 77 |
| 90% CI | 66–96 | 68–94 | 65–90 |
| Ratio of Metformin in Product of Example 4 to Glucophage ® | 78.5 | 81 | 77 |
| 90% CI | 65–94 | 70–94 | 67–70 |

EXAMPLE 8

The procedure of Example 7 was repeated except that the test formulation used was the metformin liquid of Example 5 (5 mL) of 100 mg/mL). The results were compared to those obtained with a 500 mg tablet of Glucophage®. The results are tabulated hereinbelow.

RESULTS (N=8)

|  | $C_{MAX}$ | AUCO-t | AUCO-inf. |
|---|---|---|---|
| Ratio of Metformin in Product of Example 5 to Glucophage ® | 85.98 | 87.87 | 87.26 |
| 90% CI | 73.21–100.96 | 77.77–104.66 | 73.94–102.97 |

Thus, the present liquid formulation can be taken by subjects who are fasting for several hours for various reasons, including religious reasons, and the chance of suffering from the side effects is minimized. However, the advantages of the liquid formulation relative to the solid formulation is especially realized when the stomach is empty. Normally, the stomach is emptied within an hour after ingestion of a normal meal. After the patient has consumed the meal and the stomach is empty, it is advantageous to administer the liquid formulation rather then the solid tablet. More specifically, as indicated herein above, when the liquid formulation is administered to a patient having a substantially empty stomach less metformin or its pharmaceutically acceptable salt is absorbed from the gastrointestinal tract. Although the patient is receiving the appropriate doses when taking the liquid formulation, the patient is at less risk of suffering the adverse effects of metformin or its pharmaceutically acceptable salts as compared to the administration thereof in the solid form. When using the liquid metformin of the present invention, one does not see the wide variation in the plasma profile that one would observe with the solid dosage form.

The liquid formulation not only makes the administration easier, but is definitely better and safer than the solid form thereof—the tablets.

Another advantage of the present liquid formulation is that the titration of the dosage thereof is much simpler, accurate and reproducible relative to the solid dosage form. For example, if the liquid formulation is available in 100 mg/mL strength, to administer a dose of 50 mg, all that is required is to dispense 0.5 mL which can easily be measured. If 1000 mg is to be administered, all that is required is to dispense 10 mL. However, the same flexibility is not available in solid oral dosage forms. Presently the amount commercially available in solid dosage form of metformin are 500 mg, 850 mg and 1000 mg per tablet. If a patient needs to be administered metformin in dosage amount less than that present in the tablets available, it is much more difficult to obtain the correct dosage amount, unless it matches that which is commercially available. If not, he would have to break the tablet; but he can only approximate the appropriate amount, especially since it is difficult to break the tablet uniformly and since a scale or other apparatus for weighing such small amounts is usually not present in the patient's home. As a result, the patient will be administered the metformin in solid form in an amount which may be too high or too low. Therefore, with solid dosage oral forms, there is a greater potential that the patient may receive inappropriate dosing.

The liquid pharmaceutical composition of the present invention is completely safe for administration to the animal, e.g. human and is stable for oral administration throughout the shelf life.

The above preferred embodiments and examples are given to illustrate the scope and spirit of the present invention.

The embodiments and examples described herein will make apparent to those skilled in the art other embodiments and examples.

These other embodiments and examples are within the contemplation of the present invention. Therefore, the present invention should be limited only by the appended claims.

What is claimed is:

1. A liquid pharmaceutical composition for oral administration which comprises a therapeutically effective amount of metformin or its pharmaceutically acceptable salt; a sweetener that does not increase the blood glucose level of a subject after ingestion thereof; a polyhydroxy alcohol present in an amount of about 15 to about 55% by weight; a mineral acid and bicarbonate salt both present in sufficient amounts to maintain the pH of the composition in the range of about 4.0 to about 9.0; and a pharmaceutically acceptable liquid carrier.

2. The liquid pharmaceutical composition according to claim 1, where the pharmaceutically acceptable carrier is water.

3. The pharmaceutical composition of claim 1 wherein the sweetener is present in amounts ranging from about 50% to about 70% by weight.

4. The liquid pharmaceutical composition of claim 3, wherein the sweetener is present in amounts ranging from about 55% to about 65% by weight.

5. The liquid pharmaceutical composition of claim 1, further comprising alkyl hydroxyethylcellulose.

6. The liquid pharmaceutical composition of claim 5, wherein the alkyl hydroxyethylcellulose is present in amounts ranging from 0.08% to about 0.2% by weight.

7. The liquid pharmaceutical composition of claim 1, wherein the polyhydroxy alcohol is present in amounts ranging from about 15% to about 40% by weight.

8. The liquid pharmaceutical composition of claim 5, wherein the alkyl group in alkyl hydroxyethylcellulose contains 2 to 10 carbon atoms.

9. The liquid pharmaceutical composition of claim 1, wherein the sweetener is a sugar alcohol or non-nutritive sweetener.

10. The liquid pharmaceutical composition of claim 1, wherein the polyhydroxy alcohol contains 2 to 6 carbon atoms and contains 2 to 6 hydroxy groups.

11. The liquid pharmaceutical composition of claim 1, wherein the polyhydroxy alcohol is a polymer having a molecular weight ranging from 200 to 2000 daltons and has a repeating unit of 2 to 6 carbon atoms and the repeating unit contains 2 to 6 hydroxy groups.

12. The liquid pharmaceutical composition according to claim 1 wherein the mineral acid is hydrochloric acid, nitric acid, or sulfuric acid.

13. The liquid pharmaceutical composition according to claim 12 herein the mineral acid is hydrochloric acid.

14. The liquid pharmaceutical composition according to claim 1 herein the pH ranges from about 4.2 to about 7.0.

15. The liquid pharmaceutical composition according to claim 1 wherein the bicarbonate salt is potassium bicarbonate.

* * * * *

UNITED STATES PATENT AND TRADEMARK OFFICE
CERTIFICATE OF CORRECTION

PATENT NO. : 6,890,957 B2
DATED : May 10, 2005
INVENTOR(S) : Chandran et al.

It is certified that error appears in the above-identified patent and that said Letters Patent is hereby corrected as shown below:

Title page,
Item [56], References Cited, U.S. PATENT DOCUMENTS, "3/1965 Matheson" should read -- 3/1962 Matheson --.

Column 3,
Lines 33 and 34, "patent" should read -- patient --.

Column 5,
Line 24, "singly" should read -- singularly --.

Column 8,
Line 27, "thiazolinedione" should read -- thiazolidinedione --.

Column 12,
Line 40, "Bristol Meyers" should read -- Bristol-Myers --.
Line 41, "hyrdrochloride" should read -- hydrochloride --.

Column 14,
Line 65, "100 mg/mL)." should read -- 100 mg/mL. --.

Signed and Sealed this

Sixth Day of September, 2005

JON W. DUDAS
*Director of the United States Patent and Trademark Office*